United States Patent [19]
Ito et al.

[11] Patent Number: 5,422,255
[45] Date of Patent: Jun. 6, 1995

[54] METHOD FOR PRODUCING D-ALANINE

[75] Inventors: Noriko Ito; Shinzo Imamura; Haruyo Sato, all of Aichi, Japan

[73] Assignee: Toray Industries, Inc., Japan

[21] Appl. No.: 27,551

[22] Filed: Mar. 5, 1993

Related U.S. Application Data

[63] Continuation of Ser. No. 614,982, Jan. 11, 1991, abandoned, which is a continuation-in-part of Ser. No. 269,183, Nov. 18, 1988, abandoned.

[30] Foreign Application Priority Data

Feb. 13, 1987 [JP] Japan .................. 62-29709

[51] Int. Cl.[6] .................. C12P 13/06; C12N 1/16
[52] U.S. Cl. .................. 435/116; 435/255.1; 435/254.1; 435/911; 435/938; 435/921; 435/944
[58] Field of Search .............. 435/116, 921, 930, 938, 435/931, 944, 911, 255.1, 254.1

[56] References Cited

U.S. PATENT DOCUMENTS 4,783,404 11/1988 Aretz et al. .................. 435/135

FOREIGN PATENT DOCUMENTS 020683 10/1967 Japan .................. 435/116

OTHER PUBLICATIONS

ATCC Catalogue of Fungi, 1987 p. 73.
ATCC Catalog of Fungi, 1987, 17th ed, pp. 123, 184, 290, 381.
Chemical Abstracts, vol. 67 1967 #9 42581d "Preparation of optically active alanine from DL-alanine by yeast" Oshima et al. *Hakko to Taisha* No. 15 89–94 discussion 94 (1967) (Japan).

*Primary Examiner*—Irene Marx
*Attorney, Agent, or Firm*—Austin R. Miller

[57] ABSTRACT

A high concentration of DL-alanine can be supplied in a culture medium and D-alanine can be efficiently obtained with high yield for a short time by cultivating a yeast which belongs to the genus Candida, the genus Cryptococcus, the genus Hansenura or the genus Trichosporon and has an ability to assimilate L-alanine and not to assimilate substantially D-alanine in a culture medium containing substantially DL-alanine as a single carbon source and a single nitrogen source under an acidic condition. Moreover, because very little other organic by-product and organic impurity exists in the culture medium when the cultivation is completed, it becomes easy to separate and refine the D-alanine.

2 Claims, No Drawings

METHOD FOR PRODUCING D-ALANINE

This application is a continuation of application Ser. No. 614,982 filed Jan. 11, 1991, now abandoned, which was a continuation-in-part of application Ser. No. 269,183 filed Nov. 18, 1988, now abandoned.

FIELD OF THE INVENTION

The present invention relates to a method for producing D-alanine by fermentation.

DESCRIPTION OF THE PRIOR ART

A method for producing D-alanine by cultivating a yeast in a medium containing both glucose and the like and DL-alanine is disclosed in "Amino Acid and Nucleic Acid", 15, 89–94(1967). A method for producing about equal amounts of D-alanine and pyruvic acid in parallel by using a microorganism having capability for oxidizing L-alanine from both glucose and the like and DL-alanine has been disclosed in Japanese Examined Patent Publication No.20683/1967.

Both conventional methods are excellent as methods for obtaining expensive D-alanine with high purity from inexpensive DL-alanine.

However, in the cited literature, it was clearly disclosed that if the concentration of DL-alanine is 20 g/l or more, not only was the growth of strains obstructed, but also the capability of selectively decomposing decreased. Namely, when the concentration of the raw material DL-alanine is limited to below 20 g/l, the yield of D-alanine is at most only 10 g/l even if a theoretically quantitative amount can be achieved and therefore it is not an industrially favorable method.

In the latter method, the concentration of DL-alanine was at most 50 g/l and the yield of D-alanine was also low, namely, at most 17 g/l. The time required for cultivating strains and oxidizing L-alanine was long, namely, 72 hours in all and this method is not an industrially efficient method either.

Moreover, in the latter method, it is necessary to separate and remove a large amount of pyruvic acid for obtaining D-alanine and therefore it is industrially unfavorable.

DISCLOSURE OF INVENTION

The present inventors have been extensively studying to solve the above described problems and to offer an industrially favorable method for producing D-alanine effective to obtain D-alanine having an accumulated concentration of scores of grams/l or more, by cultivating a specific yeast in a culture medium containing a specific carbon source and a specific nitrogen source.

A purpose of the present invention is to provide a method for producing D-alanine with high yield, namely with almost a theoretically quantitative amount from DL-alanine by a selective assimilation method using a microorganism.

Another purpose of the present invention is to provide a method for producing D-alanine with high yield by supplying a high concentration of DL-alanine to a culture medium without obstructing the growth of strains and without decreasing the capability of selective decomposition.

Another purpose of the present invention is to offer a method in which very few organic byproducts and organic impurities exist in the culture medium when the cultivation is completed.

Another purpose of the present invention is to offer an efficient method in which the time required for cultivating and assimilating DL-alanine can be shortened.

These and other purposes of the present invention are clarified by the following detailed explanation.

These purposes can be achieved by a method for producing D-alanine comprising the steps of cultivating a yeast which belongs to the genus Candida, Pichia, Cryptococcus, Hansenula or Trichosporon and which yeast has an ability to assimilate L-alanine and not to assimilate substantially D-alanine in a medium containing substantially DL-alanine as a single carbon source and a single nitrogen source and by obtaining D-alanine from the cultivated substance.

DESCRIPTION OF THE PREFERRED EMBODIMENT OF THE INVENTION

The present invention is hereinafter described in detail.

As the yeast used in the present invention, yeasts belonging to the genus Candida, Pichia, Cryptococcus, Hansenula or Trichosporon can be cited. Among these yeasts, such yeasts that can grow in a medium containing substantially DL-alanine as a single carbon source and a single nitrogen source and at the same time have an ability to assimilate L-alanine and not to assimilate substantially D-alanine can be used in the present invention.

In the present invention, a yeast which does not substantially assimilate D-alanine is intended to include such a yeast which does assimilate only small amount of D-alanine, to the extent that the effect of the present invention is not substantially obstructed, or a yeast which does assimilate D-alanine in the absence of L-alanine after the L-alanine has been completely assimilated.

For example, *Candida humicola* ATCC 36992, (*Apiotrichum humicola* ATCC 36992), *Candida rugosa* ATCC 10571, *Candida rugosa* ATCC 20306 (*Saccharomycopsis lipolytica*), *Cryptococcus laurentii* ATCC 36832, *Candida famata* ATCC 20284 (*Torulopsis candida*), *Candida glabrata* IFO 0005 (*Torulopsis glabrata*), *Pichia burtonii* ATCC 20279 (*Hypopichia burtonii* ATCC 20279), *Pichia pastoris* IFO 0948, *Hansenula polymorpha* ATCC 26012, *Hansenula capsulata* ATCC 16753 or, *Trichosporon beigelii* ATCC 36993 may be employed. The ATCC number is the registration number of the deposit in the American Type Culture Collection (ATCC). The ATTC is located at 12301 Parklawn Drive, Rockville, Md., 20852, USA.

In the present invention, the cultivation is carried out in a medium containing substantially DL-alanine as a single carbon source and a single nitrogen source. Namely, in the present invention, as a carbon source and a nitrogen source in a medium, DL-alanine is substantially used. Therefore, the cultivation can be carried out in the absence of the other carbon source and nitrogen source or in the presence of less than 1 weight part of the other carbon source and nitrogen source based on the amount of 10 weight part of DL-alanine. Preferably, the cultivation is carried out in the absence of the other carbon source. When the other carbon source and nitrogen source present in amount of not less than 1 weight part based on the amount of 10 weight part of DL-alanine, the rate of assimilation of L-alanine is low.

In the culture medium, salts of metal ion can be added according to the microorganism. As the metal ion, for example, $Na^+$, $K^+$, $Ca^{2+}$, $Mg^{2+}$, $Fe^{2+}$, $Ni^{2+}$, $Zn^{2+}$, $Co^{2+}$, $Mn^{2+}$ and so on may be used. The salts of various inorganic acids such as sulfuric acid, hydrochloric acid, phosphoric acid and so on of these metal ions can be used.

The concentration of DL-alanine in the medium is 1 to 250 g/l, preferably 60 to 200 g/l. When the concentration of DL-alanine is low, the production efficiency becomes worse. On the other hand, when the concentration is too high, the cultivation time becomes longer and there is a chance that the growing of microorganisms is arrested.

All of the DL-alanine can be fed into the culture medium from the beginning, but, if the concentration becomes too high, the growing of microorganisms becomes low and the cultivation time therefore becomes long. Accordingly, a flow-adding cultivation, in which the initial concentration is in the range of 20 to 50 g/l and the remaining DL-alanine is separately fed, is preferable.

It is preferable that the cultivation is carried out on the acidic side. In the culture medium pH is usually adjusted to 5 when the cultivation starts, but the pH increases as the cultivation proceeds. Because the rate of recovery of D-alanine decreases if the cultivation is left as it is, it is necessary to adjust the pH to the acidic side.

As the reason why the rate of recovery of D-alanine decreases if the pH changes to the alkaline side, it is considered that D-alanine is assimilated by the fact that alanine racemase or D-alanine-aminotransferase is activated.

Based on these reasons, the pH during cultivation is usually adjusted to 4 to 6.5, preferably 4.5 to 6.0. As the acid for the adjustment, for example, an aqueous solution of an inorganic acid such as phosphoric acid, sulfuric acid, hydrochloric acid and or the like is preferable.

In the above described literature, "Amino Acid and Nucleic Acid", it was indicated a conclusion in its abstract that selective decomposition occurred on the high pH side during cultivation and the selectivity rather became worse on the low pH side. For example, in FIG. 4 in the above described "Amino acid and Nucleic Acid" reference an example indicated that selective decomposition by *Torulopsis fermeta* was completed at pH 8.5.

When the pH during cultivation is 6.5 or less, like the present invention, because ordinary bacteria hardly grow, the present invention has the advantage that contamination with saprophyte hardly occurs during cultivation.

The cultivation temperature is usually 20° to 40° C., preferably 25° to 35° C. The cultivation is carried out with stirring and aeration. The amount of aeration is usually 0.5 to 2.0 vvm, preferably 0.6 to 1.2 vvm. If the amount of aeration is too small, there is a tendency that the assimilating speed of L-alanine becomes slow. If the amount of aeration is too large, the effect does not change, and it is not desirable that the concentration of the culture medium becomes higher, and vigorous foaming occurs because vaporization of the culture medium is rather accelerated.

The cultivation is usually finished when the L-alanine is wholly assimilated. Complete assimilation of L-alanine can be detected by monitoring the amount of dissolved oxygen or analysing the amount of D-isomer and L-isomer of alanine. An acid is added to neutralize ammonia produced by assimilation of L-alanine during cultivation, but the addition of the acid becomes unnecessary after assimilation of L-alanine is completed. Therefore, this can be also detected by monitoring the amount of acid added.

Because D-alanine is also gradually assimilated after the L-alanine has been wholly assimilated, in some cases it is desirable that the end point of the cultivation is clearly detected.

After removing cells from the culture broth thus obtained by means of centrifugal separation methods D-alanine is separated by the usual methods.

For example, alanine is adsorbed with an ion-exchange resin "SK-1B" (manufactured by Mitsubishi Chemical Industries Co., Ltd.) by passing the medium through the resin and thereafter thoroughly washing. Then, alanine is eluted with an ammonia aqueous solution and the eluate is concentrated. Refined D-alanine can be obtained by recrystallizing the crude D-alanine thus obtained with water.

The present invention exhibits the following effects.
(1) D-alanine can be obtained in high yield, namely in an almost theoretically quantitative amount from DL-alanine.
(2) Moreover, D-alanine can be obtained in high yield by supplying a high concentration of DL-alanine to a culture broth without obstructing the growth of strains and without decreasing the capability of selective decomposition.
(3) Moreover, L-alanine having been consumed is almost converted into carbon dioxide and water and neither an organic by-product nor an organic impurity exists substantially in the culture broth. It is therefore easy to separate and refine the resulting D-alanine.
(4) D-alanine can be efficiently produced, as the time required for cultivating and assimilating DL-alanine can be shortened.
(5) Because the cultivation is carried out under an acidic condition at pH 6.5 or less, contamination with saprophyte hardly occurs during cultivation.

The present invention is hereinafter explained by reference to examples.

In the examples, the DL analysis of alanine is carried out by High Performance Liquid Chromatography (hereinafter referred to as "HPLC"). The sample is prepared by esterifying alanine in powder with methanol-hydrochloric acid and reacting with 3,5-dinitrophenylisocyanate. The analysing conditions of HPLC are as follows;
Column: OA-1000 (Sumitomo Chemical Co., Ltd.)
Mobile phase: n-Hexane:Dichloromethane:Ethanol (20:8:1)
Flow rate: 1 ml/min
Detector: UV 254 nm

EXAMPLE 1

50 ml of a medium containing 30 g/l of dried bouillon (pH 6.0) were dividedly poured into an 1 l Erlenmeyer flask and sterilized at 120° C. for 20 minutes to make a medium for cultivating species. One platinum loop of *Candida humicola* ATCC 36992 (*Apiotrichum humicola* ATCC 36992) was inoculated on the medium and was cultivated with shaking at 30° C. for a day. On the other hand, 1 l of a medium (pH 5.0) containing 100 g/l of DL-alanine, 2 g/l of potassium hydrogenphosphate, 0.5 g/l of magnesium sulfate and 0.5 g/l of powder yeast extract was put into a 3 l minijar fermenter and sterilized to make a main culture medium. The above described culture broth was inoculated on it and was cultivated with stirring and aeretion at 1.0 vvm at 30° C. During the cultivation, the pH was adjusted at 5.0±0.1 with 2N sulfuric acid. L-alanine was wholly assimilated for about 70 hours and 1.2 liter of the culture broth containing 48 g of D-alanine, 35 g of ammonium sulfate was obtained.

After removing cells from this culture broth by means of a centrifugal separator at 10,000 rpm for 10 minutes, D-alanine was absorbed on an ion-exchange resin SK-1B (H type) by passing the medium through a column packed with the resin. After washing column throughly with water, D-alanine was eluted with 4% ammonia aqueous solution. This eluate was concentrated under reduced pressure to obtain 45 g of D-alanine. The optical purity was 99.6% ee or more on analysis by means of HPLC. The chemical purity was 99.4%.

EXAMPLE 2

In this case, among the procedures shown in Example 1, the concentration of DL-alanine in the main culture medium was changed to 80 g/l and the others were the same as those of Example 1. The cultivation was finished after about 35 hours and about 1.2 l of the culture broth containing 38 g of D-alanine and 28 g of ammonium sulfate were obtained.

After removing cells from this culture broth by means of a centrifugal separator, a salt exchanging operation was carried out by adding and stirring 18.3 g of calcium hydroxide for about 2 hours. This suspension was concentrated under reduced pressure to one third of the original amount and thereafter filtered to remove inorganic salts. A slight amount of metallic ion was absorbed on an ion-exchange resin SK-1B (ammonium type) by passing the filtrate through a column packed with the resin. After combining eluate and the washing liquid of the column, the combined solution was concentrated to crystallize D-alanine out. 32 g of refined D-alanine were thus obtained.

The optical purity of the product and the chemical purity were 99.9% ee and 99.9% respectively.

EXAMPLE 3

50 ml of a medium (pH 5.0) containing 20 g/l of DL-alanine, 2 g/l of potassium hydrogenphosphate, 0.5 g/l of magnesium sulfate and 0.5 g/l of powdered yeast extract were dividedly poured into a 1 l Erlenmeyer flask and sterilized to make a medium for cultivating species. One platinum loop of Candida humicola ATCC 36992 (Apiotrichum humicola ATCC 36992) was inoculated on this medium and was cultivated while shaking at 30° C. for about 24 hours. On the other hand, 1 liter of a culture medium whose composition was the same as the above described one, except that the amount of DL-alanine was 40 g/l, was put into a 3 liter minijar fermenter and sterilized to make a main culture medium. The above described culture broth was inoculated and was cultivated with stirring and aeration at 1.0 vvmat 30. During cultivation, the pH was adjusted to 5.0±0.1 with 2N sulfuric acid. After about 20 hours when about 80% of the L-alanine in the culture medium had been assimilated, this culture broth was inoculated by a 5% seed on 1 liter of a new main culture medium having the same constituting components and cultivated with stirring and aeration under the same conditions as the preceding one. After cultivation was carried out for about 20 hours, this culture broth was then inoculated by a 5% seed in 1 liter of a main culture medium having the same components as the preceding one except that the concentration of DL-alanine was 80 g/l. After cultivation was carried out with stirring and aeration under the same conditions for about 60 hours, the L-alanine in the culture broth was wholly assimilated. After the cultivation was finished, the yield, optical purity and chemical purity of the D-alanine obtained by the same procedures as shown in Example 2 were almost the same values as those of Example 2.

EXAMPLE 4

Among the procedures shown in Example 1, the main culture medium was changed to 700 ml of a culture medium containing 55 g of DL-alanine, 2 g of potassium hydrogen-phosphate, 0.5 g of magnesium sulfate and 1 g of powdered yeast extract and the cultivation was carried out under the same conditions as those of Example 1. After about 20 hours, addition of 300 ml of aqueous solution containing 45 g of DL-alanine was started with a flow rate of 15 ml/hr. After the addition for about 20 hours was finished, the cultivation was further continued. After about 60 hours from the beginning of the cultivation, the cultivation was completed.

The yield, optical purity and chemical purity of D-alanine obtained from the culture broth by the same procedures as those of Example 1 were the same as those of Example 1.

EXAMPLES 5 to 14

5 ml of a culture medium for the species shown in Table 4 (pH 5.0) comprising 30 g/l of dried bouillon were dividedly poured into the test tubes of 18×180 mmφ and sterilized. One platinum loop of each yeast shown in Table 1 was inoculated in this medium and cultivated while shaking at 30° C. for 1 to 2 days. On the other hand, 5 ml of a main culture medium (pH 5.0) comprising 10 g/l of DL-alanine, 2 g/l of potassium hydrogen phosphate, 0.5 g/l of magnesium sulfate and 0.5 g/l of powdered yeast extract were dividedly poured into the test tubes of 18×180 mmφ and sterilized. The above described culture media for species were inoculated 5% seeds and cultivated while shaking at 30° C. After 24 hours, cells were removed from these culture broths by means of a centrifugal separator and the solutions were concentrated under reduced pressure, evaporated to dryness and dried. Remaining percentages of remaining L- and D-alanine were determined by means of HPLC on the solids thus obtained.

The results obtained were shown in Table 1.

TABLE 1

| Example | Strain | Disposition No. | Remaining Alanine L (%) | Remaining Alanine D (%) |
|---|---|---|---|---|
| 1–5 | Candida humicola (Apiotrichum humicola) | ATCC 36992 | 2.0 | 97.4 |
| 6 | Candida rugosa | ATCC 10571 | 6.0 | 99.1 |
| 7 | Candida rugosa (Saccharomycopsis lipolytica) | ATCC 20306 | 28.6 | 99.0 |
| 9 | Cryptococcus laurentii | ATCC 36832 | 39.0 | 100.0 |
| 10 | Candida famata (Torulopsis candida) | ATCC 20284 | 17.1 | 97.1 |
| 11 | Pichia burtonii (Hypopichia burtonii) | ATCC 20279 | 25.9 | 98.5 |
| 13 | Hansenula polymorpha | ATCC 26012 | 37.7 | 95.5 |
| 14 | Trichosporon beigelii | ATCC 36993 | 33.5 | 87.5 |

COMPARISON EXAMPLE

A cultivation was carried out under the same conditions as the procedures shown in Example 2 except that 10 g/l of glucose was added to the main culture medium. The cultivation was finished after about 54 hours and about 1.2 l of the culture medium containing 32 g of D-alanine and 29 g of ammonium sulfate. The solid obtained by treating 50 ml of this culture medium with the same procedures as those of Example 5 to 14 was analyzed by means of HPLC and the optical purity of D-alanine thus obtained was found to be 99.6% or more.

INDUSTRIAL UTILIZALILITY

D-alanine is useful for medical raw materials or as a raw material of sweetening "Alitheme".

We claim:

1. A method for producing D-alanine comprising the steps of:
   (a) cultivating a yeast selected from the group consisting of *Candida rugosa* ATCC 10571, *Saccharomycopis lipolytica* ATCC 20306, *Candida famata* ATCC 20284, *Cryptococcus laurentii* ATCC 36832, *Hansenula polymorpha* ATCC 26012 and *Trichosporon beigelii* ATCC 36993, that has the ability to assimilate L-alanine and cannot assimilate D-alanine, in a nutrient medium containing DL-alanine as a source of carbon and nitrogen at pH 4.0 to 6.5, wherein said nutrient medium contains no other sources of carbon and nitrogen or contains less than 1 weight part of other sources of carbon and nitrogen per 10 weight parts of DL-alanine, and
   (b) recovering D-alanine from the culture broth.

2. A method for producing D-alanine comprising the steps of:
   (a) cultivating a yeast selected from the group consisting of *Apiotrichum humicola* ATCC 36992 and *Hypopichia burtonii* ATCC 20279, that has the ability to assimilate L-alanine and cannot assimilate D-alanine, in a nutrient medium containing DL-alanine as a source of carbon and nitrogen at pH 4.0 to 6.5, wherein said nutrient medium contains no other sources of carbon and nitrogen or in the presence of less than 1 weight part of other sources of carbon and nitrogen per 10 weight parts of DL-alanine, and
   (b) recovering D-alanine from the culture broth.

* * * * *